(12) United States Patent
Seo et al.

(10) Patent No.: US 7,622,577 B2
(45) Date of Patent: Nov. 24, 2009

(54) PROCESSES FOR THE PREPARATION OF CEPHALOSPORIN DERIVATIVES

(75) Inventors: Dae Won Seo, Gunpo (KR); In Hwa Chung, Yongin (KR); Ki Bong Lee, Cheongju (KR); In Kyu Lee, Gunpo (KR)

(73) Assignee: CJ Cheiljedang Corporation, Seoul (KR)

( * ) Notice: Subject to any disclaimer, the term of this patent is extended or adjusted under 35 U.S.C. 154(b) by 336 days.

(21) Appl. No.: 10/577,551

(22) PCT Filed: Oct. 30, 2004

(86) PCT No.: PCT/KR2004/002771

§ 371 (c)(1),
(2), (4) Date: Apr. 28, 2006

(87) PCT Pub. No.: WO2005/042544

PCT Pub. Date: May 12, 2005

(65) Prior Publication Data

US 2007/0083042 A1      Apr. 12, 2007

(30) Foreign Application Priority Data

Oct. 30, 2003      (KR) .................. 10-2003-0076360

(51) Int. Cl.
    C07D 501/22      (2006.01)
(52) U.S. Cl. .......................................... 540/215
(58) Field of Classification Search ................ 540/215
    See application file for complete search history.

(56) References Cited

U.S. PATENT DOCUMENTS

| 4,694,079 | A | * | 9/1987 | Crast, Jr. ..................... 540/215 |
| 4,699,979 | A |   | 10/1987 | Hoshi et al. |
| 6,903,211 | B2 | * | 6/2005 | Deshpande et al. .......... 540/215 |
| 7,112,672 | B2 | * | 9/2006 | Lee et al. .................... 540/215 |

FOREIGN PATENT DOCUMENTS

| WO | 02068428 A1 | 9/2002 |
| WO | 02068438 A2 | 9/2002 |
| WO | 02083692 A1 | 10/2002 |
| WO | 03011871 A2 | 2/2003 |

OTHER PUBLICATIONS

Naito et al., "Synthesis and structure-activity relationships of a new oral cephalosporin, BMY-28100 and related compounds," J. Antibiotics, vol. 40, No. 7, 1987, pp. 991-1005.
deVroom et. al., "Synthesis of 3-alkenylcephalosporins using an epoxide mediated wittig reaction," Recl. Trav. Chim. Pays-Bas, vol. 113, 1994, pp. 305-306.

(Continued)

*Primary Examiner*—Mark L Berch
(74) *Attorney, Agent, or Firm*—Rothwell, Figg, Ernst & Manbeck, pc

(57) ABSTRACT

Provided is a process for preparing a compound of formula 1 or its salt, which comprises reacting a compound represented by the following formula 4 with acetaldehyde in a mixed solvent comprising water, isopropanol, and methylenechloride in a volume ratio of 1:3-6:11-14 in the presence of a first base to stereospecifically prepare a compound represented by the following formula 3'; and reacting the compound of the formula 3' with an anhydrous compound represented by the following formula 2 in the presence of a second base:

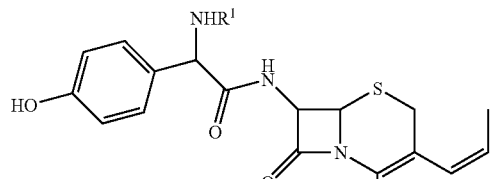

(1)

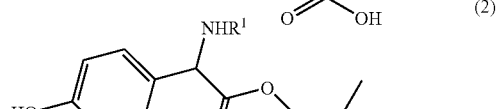

(2)

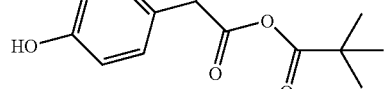

(6)

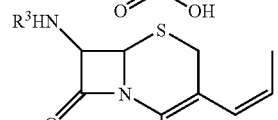

(3)'

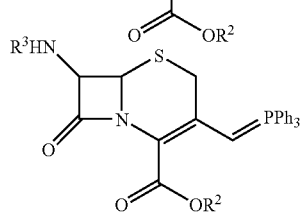

(4)

wherein $R^1$ is a hydrogen or an amino protecting group, $R^2$ is a hydrogen or a carboxyl protecting group, and $R^3$ is a hydrogen or an amino protecting group consisting of phenylacetyl group, wherein when $R^3$ is a phenylacetyl group, $R^2$ is not a hydrogen in formula 3'; and wherein, when at least one of $R^2$ and $R^3$ is a protecting group, all such protecting groups are removed from formula 3', thereby producing a compound represented by formula 6 prior to reacting it with the compound of formula 2.

6 Claims, No Drawings

OTHER PUBLICATIONS

Curini et al., "An improved procedure for the preparation of a 3-(alkenyl) cephem derivative," Gazzetta Chimica Italiana, vol. 127, 1997, pp. 195-196.

Indian Office Action issued in IN 2320/DELNP/2006 dated Mar. 17, 2009, 6 pages.

* cited by examiner

PROCESSES FOR THE PREPARATION OF CEPHALOSPORIN DERIVATIVES

CROSS REFERENCE TO RELATED APPLICATION

This application is a 35 U.S.C. § 371 National Phase Entry Application from PCT/KR2004/002771, filed Oct. 30, 2004, and designating the U.S.

BACKGROUND OF THE INVENTION

1. Field of the Invention

The present invention relates to a process for preparing cephalosporin derivatives, including cefprozil and its salt, using a 3-(Z)-propenyl cephem derivative stereospecifically prepared.

2. Description of the Related Art 3-(Z)-propenyl cephem derivative is a compound useful as an intermediate for preparation of cefprozil which is an oral cephalosporin antibiotic. Various preparation processes thereof have been known.

WO93/16084 discloses a process for selectively separating a 3-(Z)-propenyl cephem compound by means of a hydrochloride, metal, or tertiary amine salt of 7-amino-3-(1-propen-1-yl)-3-cephem-carboxylic acid or by adsorption chromatography. However, there is a disadvantage in that separation and purification are cost-ineffective.

U.K. Patent No. 2,135,305 discloses a process for preparing cefprozil from a 4-hydroxyphenylglycine compound with a t-butoxycarbonyl-protected amino group and a cephem compound with a benzhydryl-protected carboxyl group. However, incorporation of a 3-propenyl group after acylation lowers reaction efficiency and high-performance liquid chromatography is required for isomer separation, which render industrial application difficult.

U.S. Pat. No. 4,727,070 discloses a technique of removing an E-isomer cefprozil from a mixture of Z/E cefprozil, which includes incorporating an active group such as sodium imidazolidinone into the mixture of Z/E cefprozil by reaction of the mixture of Z/E cefprozil with acetone, followed by deprotection. However, purification by chromatography incurs enormous costs.

In view of the above problems, Korean Patent Laid-Open Publication No. 2002-80838 discloses a process for preparing a 3-(Z)-propenyl cephem compound by reacting a phosphoranylidene cephem compound with acetaldehyde in a mixed solvent essentially consisting of ether in the presence of a base. According to a disclosure in this patent document, ether is essentially used. In this respect, in the case of using methylenechloride, tetrahydrofuran, etc., even when other reaction conditions, for example, reaction temperature, reaction duration, base, catalyst, and the like are adjusted, it is very difficult to adjust the content of the Z-isomer to more than 83%.

Korean Patent Laid-Open Publication No. 2002-69437 discloses a 4-hydroxyphenylglycine anhydride with a pivaloyl group, which is a compound useful as an intermediate for the 7-position of cefprozil, and a preparation process thereof.

SUMMARY OF THE INVENTION

The present invention provides a process for simply preparing a cephalosporin antibiotic in high yield and purity using a 3-(Z)-propenyl cephem derivative stereospecifically prepared.

Therefore, the present invention provides a process for preparing a cephalosporin compound using a 3-(Z)-propenyl cephem derivative.

DETAILED DESCRIPTION OF THE INVENTION

According to an aspect of the present invention, there is provided a process for preparing a compound represented by the following formula 1 or its salt, which includes: reacting a compound represented by the following formula 4 with acetaldehyde in a mixed solvent including water, isopropanol, and methylenechloride in a volume ratio of 1:3-6:11-14 in the presence of a first base to stereospecifically prepare a compound represented by the following formulae 3 and reacting the compound of the formula 3 with an anhydrous compound represented by the following formula 2 in the presence of a second base:

<Formula 1>

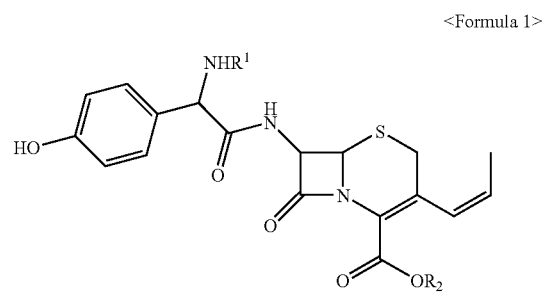

<Formula 2>

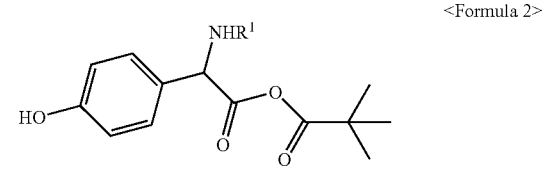

<Formula 3>

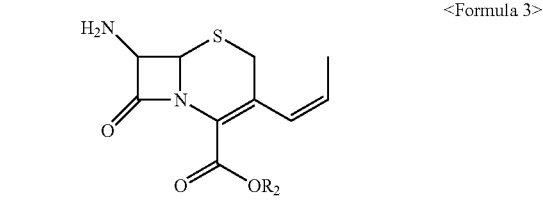

<Formula 4>

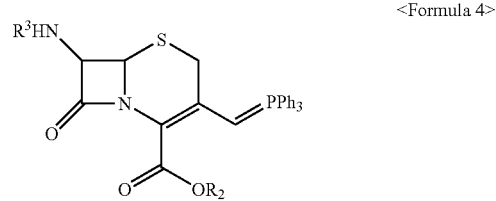

wherein $R^1$ is a hydrogen or an amino protecting group, $R^2$ is a hydrogen or a carboxyl protecting group, and $R^3$ is a hydrogen or an amino protecting group.

The salt of the compound of the formula 1 refers to a salt commonly known in the field of cephalosporin antibiotics, for example a hydrate or an acid addition salt.

As used herein, the term "stereospecific compound" refers to a mixed compound (e.g., compound of the formula 1 or 3) composed of a Z-isomer (or cis-isomer) and an E-isomer (or a trans-isomer) in a ratio of about 89-94% to about 6-11%, i.e., a compound composed of a Z-isomer and an E-isomer in a ratio of about 8.1-15.7:1.0. In this respect, the term "stereospecific preparation process" refers to a process for preparing the "stereospecific compound".

The carboxyl protecting group and the amino protecting group may be protecting groups commonly used in synthesis of cephalosporin antibiotics. Examples of the carboxyl protecting group include allyl, benzyl, p-methoxybenzyl, p-nitrobenzyl, triphenylmethyl, and diphenylmethyl, and examples of the amino protecting group include 4-methoxybenzyl, formyl, acetyl, benzyl, benzylidene, diphenylmethyl, triphenylmethyl, trichloroethoxycarbonyl, t-butoxycarbonyl, methylacetoacetate, ethylacetoacetate, and 2-ethoxycarbonyl-1-methylvinyl. Preferably, the carboxyl protecting group of $R^2$ and the amino protecting group of $R^3$ are respectively 4-methoxybenzyl and benzylcarbonyl which are commercially available. Preferably, the amino protecting group of $R^1$ is a protecting group that can be easily removed in the presence of an acid.

According to the preparation process of the present invention, when the reaction is performed in the mixed solvent including water, isopropanol, and methylenechloride in a volume ratio of 1:3-6:11-14, the compound of the formula 3 can be prepared stereospecifically, i.e., so that a Z-isomer and an E-isomer of the compound of the formula 3 are in a ratio of about 8.1-15.7:1.0 which can be seen from Table 1 of the following Examples, and the compounds of the formulae 1 and 3 can be prepared in high yield and purity. In particular, when the volume ratio of water, isopropanol, and methylenechloride in the mixed solvent is 1:4:12, the Z/E isomers with high ratio of Z/E can be obtained in high yield.

In preparation of the compound of the formula 3, the mixed solvent may be used in an amount of about 5-20 times by weight, and preferably about 10-15 times by weight, based on the compound of the formula 4. Acetaldehyde may be used in an amount of about 5-30 equivalents (eq.), and preferably about 10-15 eq., based on 1 eq. of the compound of the formula 4. The preparation of the compound of the formula 3 may be performed at a temperature of about −20 to −10° C. for about 2 to 20 hours, and preferably about 10 to 15 hours.

The compound of the formula 4 can be prepared according to a known method (e.g., Korean Patent Laid-Open Publication No. 2002-80838). That is, the compound of the formula 4 can be prepared by reacting a 3-halomethyl cephem compound represented by the following formula 5 with triphenylphosphine to obtain a phosphonium salt, followed by treatment with a third base such as sodium hydroxide or sodium carbonate:

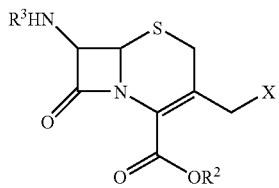

<Formula 5> wherein $R^2$ and $R^3$ are as defined in the above and X is a halogen.

The preparation of the compound of the formula 4 and the preparation of the compound of the formula 3 can be performed by one-pot reaction without separately separating the compound of the formula 4. In this case, since the base used in the preparation of the compound of the formula 4 remains in a reaction solution, there is no need to further add a base in a subsequent process, i.e., in the is preparation of the compound of the formula 3, which simplifies preparation processes.

The compound of the formula 3 can be converted to 7-amino-3-[propen-1-yl]-3-cephem-4-carboxyl acid represented by the following formula 6 by common protecting group removal:

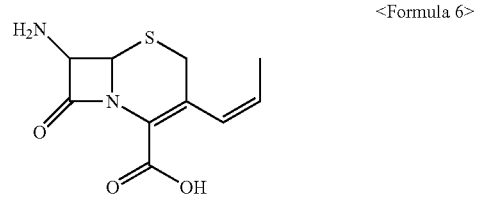

<Formula 6>

The compound of the formula 2 can be prepared according to a known method (Korean Patent Laid-Open Publication No. 2002-69437).

Preferably, the compound of the formula 2 is used in an amount of 1 to 3 eq., and preferably 1.1 to 1.5 eq., based on 1 eq. of the compound of the formula 3. Preferably, the reaction of the compound of the formula 2 with the compound of the formula 3 is performed in a mixed solvent of water with an organic solvent selected from the group consisting of dimethylsulfoxide, dimethylformamide, dimethylacetamide, 1,4-dioxane, acetonitrile, dichloromethane, and a mixture thereof. At this time, it is preferred that the content of water in the mixed solvent is 0.05 to 0.3 parts by weight, and preferably 0.1 to 0.2 parts by weight, based on 1 part by weight of the organic solvent. The reaction can be performed at a temperature of −50 to −20° C., preferably −40 to −30° C., for 1 to 4 hours, preferably 1.5 to 2.5 hours.

Examples of the second base that can be used in the reaction of the compound of the formula 2 with the compound of the formula 3 include N-methylmorpholine, triethylamine, diethylamine, n-tributylamine, N,N-dimethylaniline, and pyridine. Among them, triethylamine is preferred. Preferably, the second base is used in an amount of about 1.0 to 2.5 eq., preferably 1.1 to 1.5 eq., based on 1 eq. of the compound of the formula 2.

The entire preparation processes of the present invention can be expressed by the following reaction scheme 1:

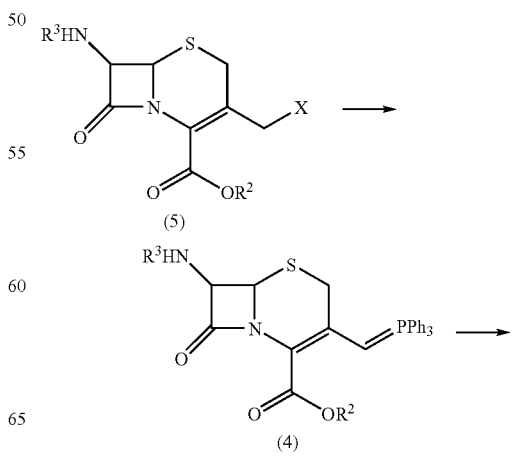

<Reaction Scheme 1>

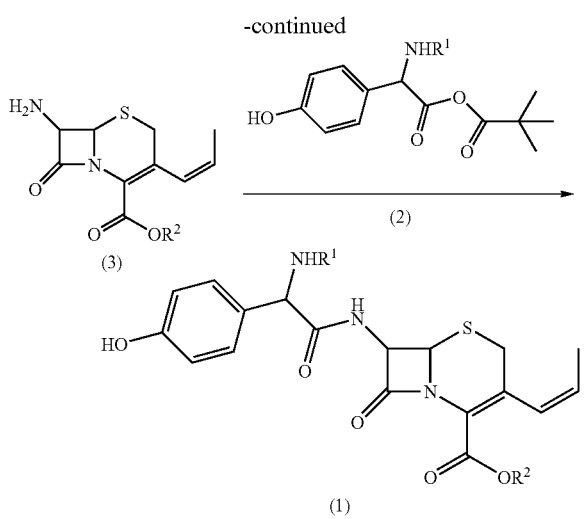

Hereinafter, the present invention will be described more specifically by Examples. However, the following Examples are provided only for illustrations and thus the present invention is not limited to or by them.

Example 1

Preparation of 7-phenylacetamido-3-[propen-1-yl]-3-cephem-4-carboxylic acid/p-methoxybenzyl ester 16 g of sodium iodide and 28 g of triphenylphosphine were added to a reactor containing 50 g (102.7 mmol) of 3-chloromethyl-7-phenylacetamido-3-[propen-1-yl]-3-cephem-4-carboxylic acid p-methoxybenzyl ester. 400 ml of methylenechloride was added thereto and stirred at 20° C. for 2 hours. After phase separation, 200 ml of a 20% sodium hydroxide solution was dropwise added to an obtained organic layer and stirred at 10° C. for 30 minutes. After separation of an organic layer, a phosphoranylidene solution was obtained.

200 ml of methylenechloride, 200 ml of isopropanol, and 50 ml of water were added to the phosphoranylidene solution and cooled to −20° C. 100 ml of acetaldehyde was dropwise added thereto and stirred for 20 hours. 30% potassium thiosulfuric acid was dropwise added and stirred for 30 minutes to separate an organic layer. 200 ml of isopropanol was dropwise added to the obtained organic layer, concentrated to produce a crystal, cooled to 0° C., and stirred for 2 hours to precipitate a solid. The solid was filtered and dried in vacuum to give 42.3 g (88.4 mmol, yield 86%, Z/E=10.1/1) of the titled compound as a white solid.

$^1$H-NMR (δ, DMSO-$d_6$): 1.52 (3H×10.1/11.1, d, (Z)-$CH_3$), 1.73 (3H×1.0/11.1, (E)-$CH_3$), 3.36-3.68 (4H, m, ph$CH_2$, C-2), 3.75 (3H, S, —$OCH_3$), 5.06-5.24 (3H, m, $CO_2$—$CH_2$, C-6), 5.52-5.69 (2H, d, —CH═CH($CH_3$), 6.06 (1H, d, —CH═CH($CH_3$), C-7), 6.91 (2H, d, ph), 7.19-7.62 (7H, m, ph)

Example 2

Preparation of 7-amino-3-[propen-1-yl]-3-cephem-4-carboxylic acid 22.8 g of phosphorous pentachloride, 150 ml of methylenechloride, and 8.88 ml of pyridine were added to a 20° C. reactor and stirred for 30 minutes. 30 g (62.6 mmol) of the 7-phenylacetamido-3-[propen-1-yl]-3-cephem-4-carboxylic acid p-methoxybenzyl ester prepared in Example 1 was dropwise added thereto, stirred for 2 hours, and cooled to −10° C. The reaction mixture was stirred for 2 hours after addition of 30 ml of 1,2-propanediol and then for 2 hours after addition of 120 ml of cresol. 200 ml of distilled water was dropwise added to the reaction solution and stirred for 1 hour. After phase separation, an aqueous layer was sent to a crystallization bath and an organic layer was extracted with 300 ml of 2N HCl and then the extract was sent to the crystallization bath. 200 ml of a 30% sodium hydroxide solution was dropwise added to the crystallization bath for crystallization and cooled to 0° C. to precipitate a solid. The solid was filtered and dried in vacuum to give 12 g (50 mmol, yield 80%, Z/E=10.1/1) of the titled compound as a beige solid.

$^1$H-NMR (δ, $D_2O$+$NaHCO_3$): 1.69 and 1.88 (3H, each, d, 6.0 Hz, —CH═CH—$CH_3$), 3.38 and 3.72 (2H, Abq, 17 Hz, H-2), 5.18 (1H, d, 5.0 Hz, H-6), 5.51 (1H, d, H-7), 5.8 (1H, m, —CH═CH—$CH_3$), 6.06 (1H, d, 11 Hz, —CH═CH—$CH_3$)

Example 3

Preparation of 7-[2-amino-2-(4-hydroxyphenyl)acetamido]-3-[propen-1-yl]-3-cephem-4-carboxylic acid (cefprozil)

Step A 75 g (0.247 mol) of potassium (2-ethoxycarbonyl-1-methyl-vinylamino)-(4-hydroxyphenyl)-acetate, 100 ml of dimethylformamide, and 10 ml of pyridine were added to a reactor and a mixed solution of 35 ml of pivaloyl chloride and 200 ml of methylenechloride was dropwise added thereto. The reaction mixture was stirred at −30° C. for 2 hours.

Step B

The reaction solution obtained in step A was cooled to −40° C. and then a solution obtained by dissolving 50 g (0.208 mol) of the 7-amino-3-[propen-1-yl]-3-cephem-4-carboxylic acid prepared in Example 2 in 200 ml of methylenechloride, 50 ml of water, and 6.5 g of triethylamine was slowly dropwise added thereto for 1 hour.

Then, the resultant solution was incubated at the same temperature for 2 hours and set to a temperature of 0° C. to obtain an insoluble solid. After the insoluble solid was filtered, a filtrate was sent to a reactor. 100 ml of 6N HCl was added thereto and stirred for 1 hour. The reaction solution was set to a pH of 3.2 by addition of 10% NaOH, stirred at 0° C. for 2 hours, and filtered to give 68.9 g (0.177 mol, 85%) of the titled compound as a white solid.

$^1$H-NMR (δ, $D_2O$-$d_2$): 1.65 (3H, d, 8.6 Hz, —CH═$CHCH_3$ (cis)), 1.81 (0.21H, d, 8.6 Hz, —CH═$CHCH_3$ (trans)), 3.22 (1H, d, 18 Hz, 2-H), 3.55 (1H, d. 18 Hz, 2-H), 5.15 (1H, d, 4.6 Hz, 6-H), 5.66 (1H, d, 4.6 Hz, 7-H), 5.75 (1H, m, vinyl-H), 5.96 (1H, m, vinyl-H), 6.91 (2H, d, 8.0 Hz, phenyl-H), 7.38 (2H, d, 8.0 Hz, phenyl-H)

Examples 4 and 5

7-phenylacetamido-3-[propen-1-yl]-3-cephem-4-carboxylic acid p-methoxy-benzyl ester was prepared in the same manner as in Example 1 except that the volume ratio of methylenechloride, isopropanol, and water was as listed in Table 1 below. The yields and Z/E isomer ratios of the compounds of Examples 1, 4, and 5 are summarized in Table 1 below.

TABLE 1

| Section | Methylenechloride (A) (ml) | Isopropanol (B) (ml) | Water (C) (ml) | Solvent ratio (A:B:C) | Yield (%) | Z/E isomer ratio |
|---|---|---|---|---|---|---|
| Example 4 | 150 | 150 | 50 | 11:3:1 | 83 | 8.9/1 |
| Example 1 | 200 | 200 | 50 | 12:4:1 | 86 | 10.1/1 |
| Example 5 | 300 | 300 | 50 | 14:6:1 | 85 | 9.1/1 |

As seen from Table 1, when a mixed solvent including methylenechloride, isopropanol, and water is used according to a solvent ratio as defined in the present invention, a 3-propenyl cephem compound of formula 3 can be stereospecifically prepared in high yield. In particular, when the volume ratio of methylenechloride, isopropanol, and water was 12:4:1, the most excellent results were obtained in terms of yield and purity.

According to the present invention, cephalosporin antibiotics, including cefprozil and its salt, can be easily prepared in high yield and purity using a 3-(Z)-propenyl cephem derivative stereospecifically prepared.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A process for preparing a compound represented by the following formula 1 or its salt, which comprises:
    reacting a compound represented by the following formula 4 with acetaldehyde in a mixed solvent comprising water, isopropanol, and methylenechloride in a volume ratio of 1:3-6:11-14 in the presence of a first base to stereospecifically prepare a compound represented by the following formula 3'; and
    reacting the compound of the formula 3' with an anhydrous compound represented by the following formula 2 in the presence of a second base:

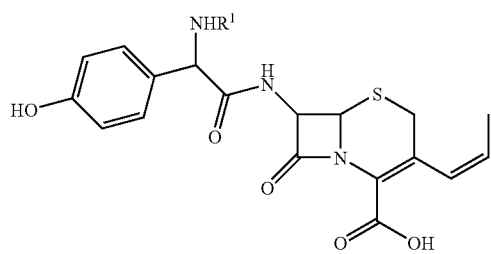

(1)

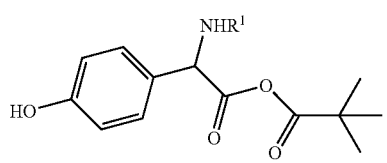

(2)

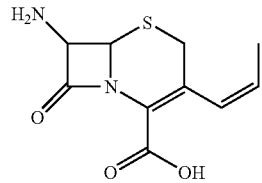

(6)

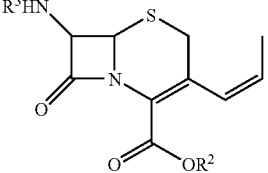

(3')

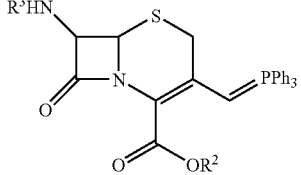

(4)

wherein $R^1$ is a hydrogen or an amino protecting group, $R^2$ is a hydrogen or a carboxyl protecting group, and $R^3$ is a hydrogen or an amino protecting group consisting of phenylacetyl group, wherein when $R^3$ is a phenylacetyl group, $R^2$ is not a hydrogen in formula 3'; and wherein, when at least one of $R^2$ and $R^3$ is a protecting group, all such protecting groups are removed from formula 3', thereby producing a compound represented by formula 6 prior to reacting it with the compound of formula 2.

2. The process of claim 1, wherein the volume ratio of water, isopropanol, and methylenechloride in the mixed solvent is 1:4:12.

3. The process of claim 1, wherein the compound of the formula 6 reacts with the compound of the formula 2 at an equivalent ratio of 1 to 1.1-1.5.

4. The process of claim 1, wherein the compound of the formula 2 reacts with the compound of the formula 6 in a mixed solvent of water with an organic solvent selected from the group consisting of dimethylsulfoxide, dimethylformamide, dimethylacetamide, 1,4-dioxane, acetonitrile, dichloromethane, and a mixture thereof.

5. The process of claim 4, wherein in the mixed solvent, water is used in an amount of 0.05 to 0.3 parts by weight, based on 1 part by weight of the organic solvent.

6. The process of claim 1, wherein the second base is selected from the group consisting of N-methylmorpholine, triethylamine, diethylamine, n-tributylamine, N,N-dimethylaniline, and pyridine.

* * * * *